(12) United States Patent
Saiki (10) Patent No.: US 7,938,030 B2
(45) Date of Patent: May 10, 2011

(54) ANALYTICAL DEVICE

(75) Inventor: Hiroshi Saiki, Ehime (JP)

(73) Assignee: Panasonic Corporation, Osaka (JP)

( * ) Notice: Subject to any disclaimer, the term of this patent is extended or adjusted under 35 U.S.C. 154(b) by 571 days.

(21) Appl. No.: 12/026,659

(22) Filed: Feb. 6, 2008

(65) Prior Publication Data

US 2009/0193913 A1 Aug. 6, 2009

(51) Int. Cl.
*G01N 1/38* (2006.01)
*G01N 35/10* (2006.01)

(52) U.S. Cl. ....... 73/864.81; 73/64.53; 422/72; 422/503

(58) Field of Classification Search ................. 73/64.53, 73/864.72, 864.81; 422/72, 100, 501–503; 436/45, 180
See application file for complete search history.

(56) References Cited

U.S. PATENT DOCUMENTS

| | | | |
|---|---|---|---|
| 3,684,450 A * | 8/1972 | Klemm et al. ................. 436/45 |
| 4,519,981 A * | 5/1985 | Guigan ....................... 422/72 X |
| 4,761,381 A * | 8/1988 | Blatt et al. .................... 436/165 |
| 4,894,204 A * | 1/1990 | Cornut ............................ 422/72 |
| 6,750,053 B1 * | 6/2004 | Widrig Opalsky et al. .......................... 435/287.9 |
| 7,854,893 B2 * | 12/2010 | Saiki et al. ...................... 422/72 |
| 2006/0228258 A1 * | 10/2006 | Samsoondar .............. 422/82.05 |

FOREIGN PATENT DOCUMENTS

| | | |
|---|---|---|
| JP | 61-167469 | 7/1986 |
| JP | 2002-514755 | 5/2002 |
| JP | 2004-212050 | 7/2004 |
| WO | WO 91/18656 | 12/1991 |
| WO | WO 99/58956 | 11/1999 |

* cited by examiner

*Primary Examiner* — Thomas P Noland
(74) *Attorney, Agent, or Firm* — Steptoe & Johnson LLP (57) ABSTRACT

An analytical device according to the present invention comprises a liquid accommodating chamber 9 for accommodating a sample solution of a quantity required for analyzing; a volume measuring chamber 10 connected to the liquid accommodating chamber 9 with a connecting path 13 and disposed in the exterior of the liquid accommodating chamber 9 in a radial direction; an overflowing chamber 11 connected to the volume measuring chamber 10 for accommodating an excessive quantity of the sample solution; and a measuring cell 12 for transferring and measuring the sample solution measured in the volume measuring chamber 10; wherein an overflowing port 14 of the volume measuring chamber 10 is connected to a flow-in port 16 of the overflowing chamber 11 by a capillary path 17.

2 Claims, 10 Drawing Sheets

ANALYTICAL DEVICE

FIELD OF THE INVENTION

The present invention relates to a rotationally driven analytical device, specifically, to the volume measurement of biological fluid using an analytical device used in the measurement of biological fluid.

BACKGROUND OF THE INVENTION

Heretofore, as a method for analyzing biological fluids, an analyzing method using a micro device wherein a liquid flow path is formed has been known. Since the micro device can control fluids using a rotating device, and can perform the measurement of samples, the separation of cytoplasmic materials, and the transportation and distribution of separated fluids using centrifugal force, various biochemical analyses can be performed.

Figure 9:
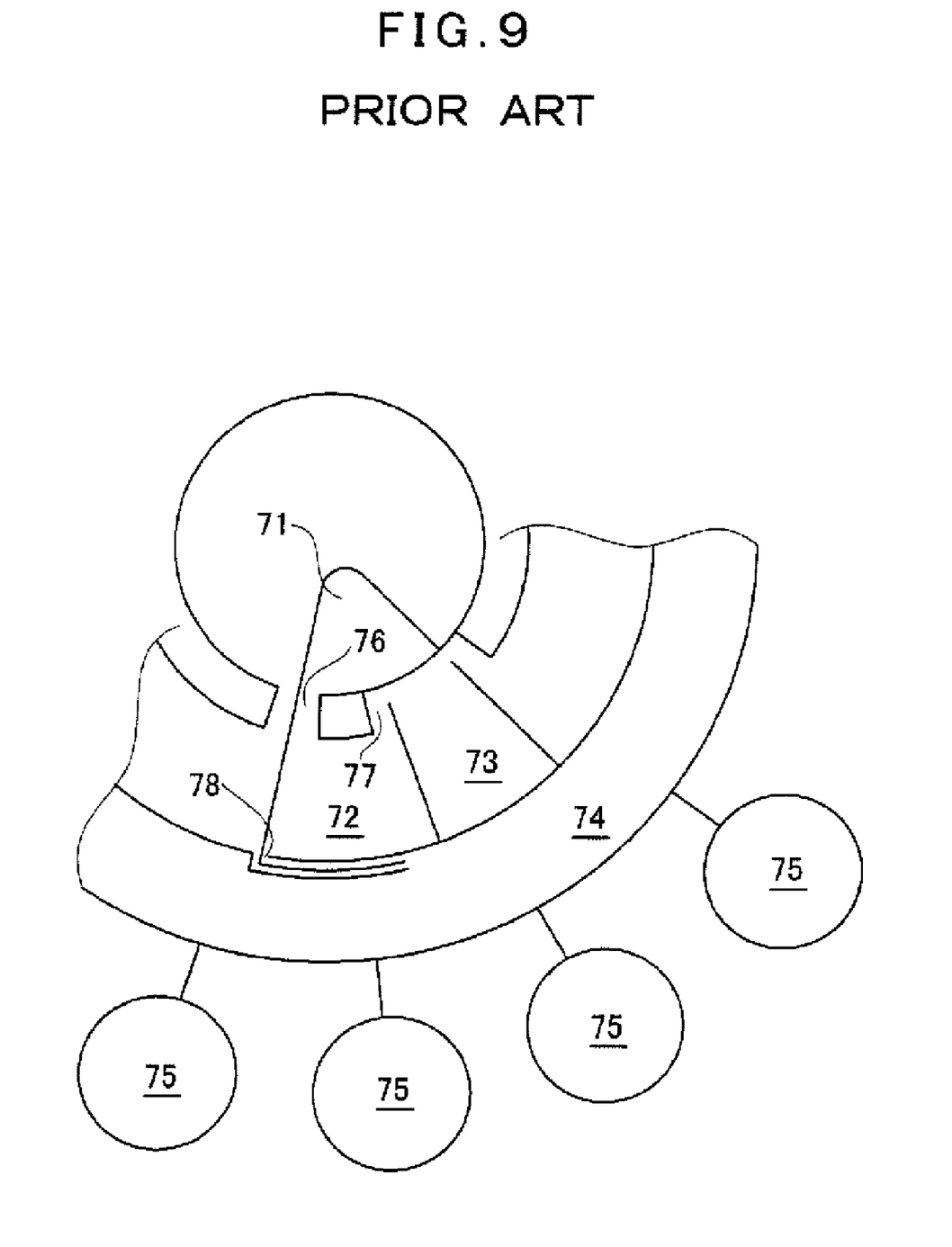
FIG. 9 is an explanatory diagram of an analytical device for measuring a sample using centrifugal force according to a conventional example.

An example of methods for measuring samples using centrifugal force is the method disclosed in Japanese Patent Laid-Open No. 61-167469. FIG. 9 shows this analytical device.

The analytical device is equipped with a central accommodating section 71 for accommodating a liquid to be diluted before analysis, a volume measuring chamber 72 and an overflowing chamber 73, a mixing chamber 74, and measuring cells 75 from the center of the analytical device toward the periphery. The volume measuring chamber 72 is located in substantially parallel with the overflowing chamber 73, and an opening 78 is formed on the wall of the volume measuring chamber facing a supplying port 76 in addition to the supplying port 76 and an overflowing port 77. The opening 78 is always open, and has a cross section much smaller than the cross sections of the supplying port 76 and the overflowing port 77.

With such a configuration, the volume measuring chamber 72 can be quickly filled, and the overflow can be immediately removed. When the volume measuring chamber 72 starts to be filled with a liquid, the liquid immediately starts flowing out of the chamber. Therefore, since the ratio of "supplying time," to "flow-out time from the flow-out port", which is a function of the ratio of "cross-sectional area of the flow-in port" to "cross-sectional area of the flow-out port", can be reduced, accuracy is added to measurements.

Figure 10:
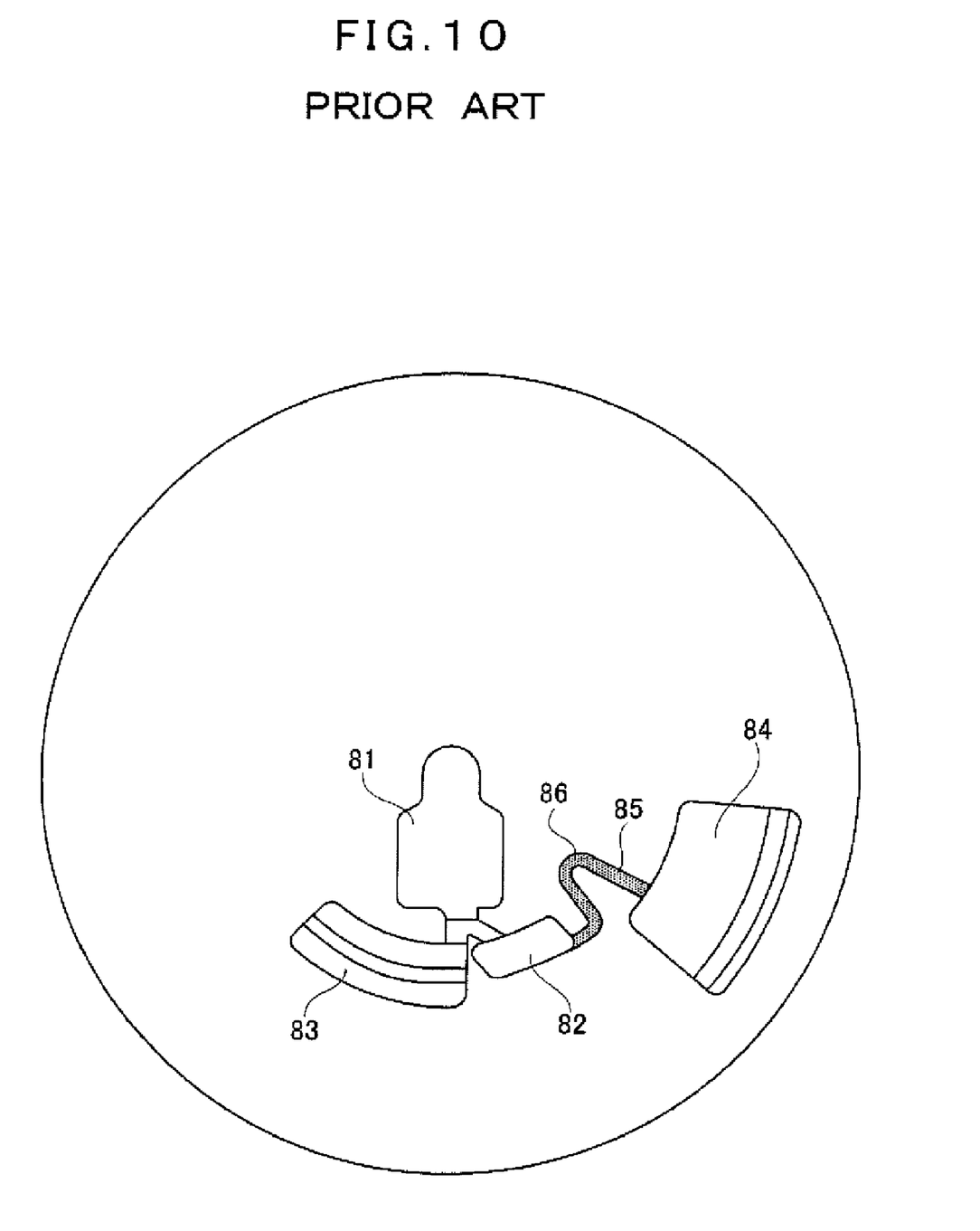
FIG. 10 is an explanatory diagram of another analytical device for measuring a sample using centrifugal force.

In National Publication of International Patent Application No. PCT/US91/03840, which was published as WO91/18656, an analytical device shown in FIG. 10 is disclosed.

The analytical device has a fluid chamber 61, a volume measuring chamber 82 connected to the fluid chamber 81 and disposed outside the fluid chamber 81 in the radial direction, an overflowing chamber 83 connected to the volume measuring chamber 82, a receiving chamber 84 disposed outside the volume measuring chamber 82 in the radial direction, and a capillary connector 85 for supplying a liquid to the receiving chamber 84 from the volume measuring chamber 82. The capillary connector 85 has a siphon 86 having a capillary structure. Since the capillary force is smaller than the centrifugal force when the analytical device is rotationally in operation by locating the elbow-shaped bend of the siphon 86 so as to have substantially the same distance as that from the center of the analytical device to the innermost point of the volume measuring chamber 82 in the radial direction, the liquid/air interface coincides with the shape of a rotating cylinder having the same axis line as that of the volume measuring chamber 82, and also having a radius of a length equal to the distance from the center of the analytical device to the innermost point of the volume measuring chamber 82 in the radial direction, the chamber 82 is filled, and the excessive liquid flows into the overflowing chamber 83. When the operation of the analytical device is stopped, the liquid filled in the volume measuring chamber 82 flows into the capillary connector 85 by the capillary force, and when the analytical device is rotated again, the siphon is activated, and the liquid present in the volume measuring chamber 82 is discharged into the receiving chamber 84.

DISCLOSURE OF THE INVENTION

In the conventional configurations, however, since the centrifugal force is larger than the surface tension acting between a liquid and the wall of the volume measuring chamber, liquid surfaces are balanced at the opening position of the overflowing port, so that a given amount can be measured. However, when the rotation is slowed down or stopped to shift to a next process, the liquid is released from the centrifugal force, and at the same time, surface tension starts acting at the interface between the liquid and a wall surface of the overflowing port, and by the surface tension, the liquid runs along the wall surface of the overflowing port and flows into the overflowing chamber resulting in inaccurate measurements. Also since the flowing amount varies depending on the difference in properties of the liquid, the size of the volume measuring chamber must be changed depending on the liquids to be analyzed.

To solve such conventional problems, it is an object of the present invention to provide an analytical device that can accurately weigh a liquid.

To solve the problems in the conventional devices, an analytical device according to the present invention comprises a liquid accommodating chamber for accommodating a sample solution of a quantity required for analyzing; a volume measuring chamber keeping a specified quantity of the sample solution, connected to the liquid accommodating chamber with a connecting path, and disposed in the exterior of the liquid accommodating chamber in a radial direction; an overflowing chamber connected to the volume measuring chamber for accommodating a quantity of the sample solution exceeding the specified quantity; and a measuring cell for transferring the sample solution measured in the volume measuring chamber and measuring the sample solution; wherein an overflowing port of the volume measuring chamber is connected to a flow-in port of the overflowing chamber by a capillary path.

According to the analytical device of the present invention, by connecting the volume measuring chamber to the overflowing chamber with a capillary path, since a liquid held in the volume measuring chamber by rotating the analytical device is trapped in the capillary path and does not flow into the overflowing chamber even if the rotation of the analytical device is slowed down or stopped to shift to the following step, the liquid can be accurately measured. Also since a liquid with different surface tension does not flow into the overflowing chamber after measuring, the same quantity of the liquid can be measured.

DESCRIPTION OF THE EMBODIMENT(S)

Embodiments of the present invention will be described referring to FIGS. 1 to 8.

First Embodiment

FIGS. 1 to 4D show the first embodiment of the present invention.

Figure 1:
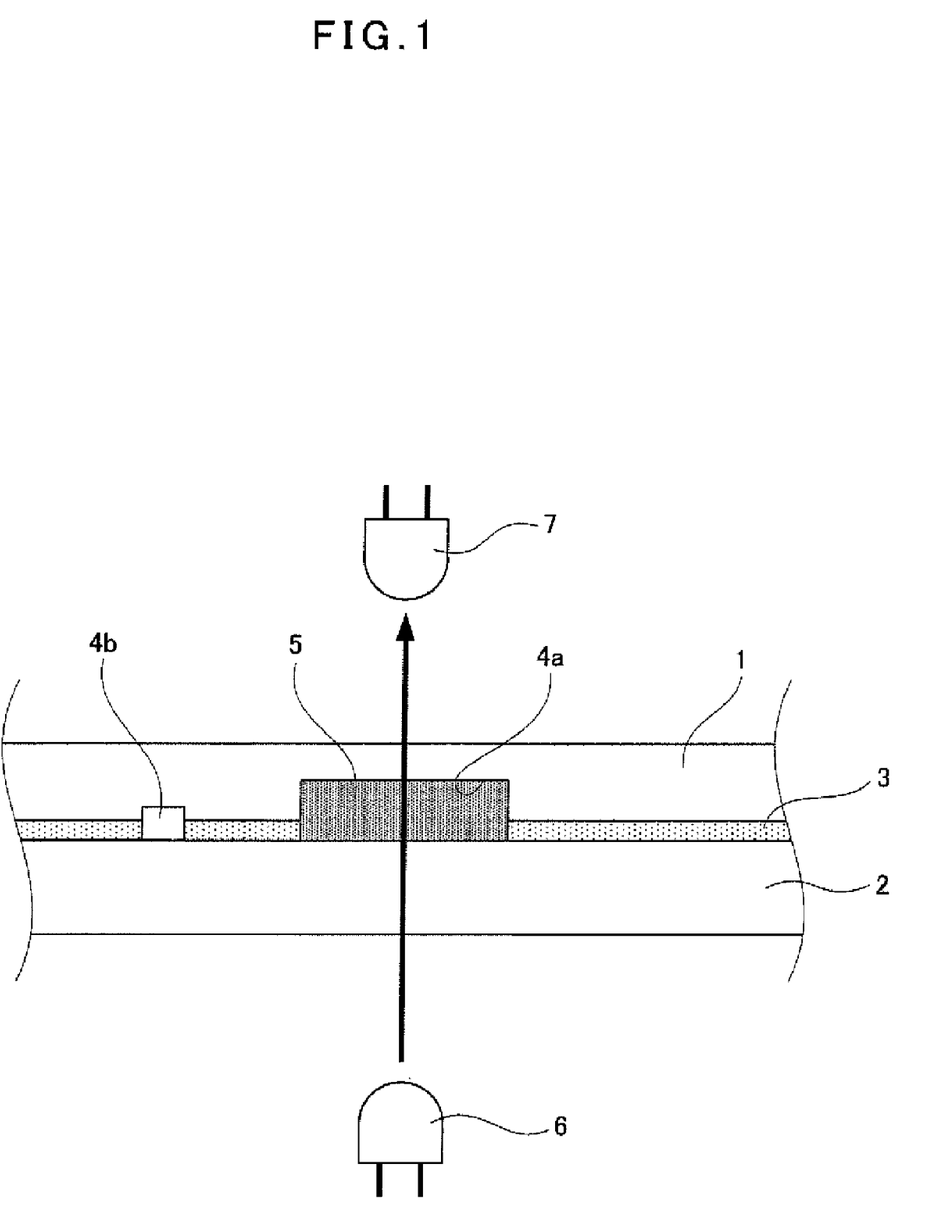
FIG. 1 is an enlarged sectional view of an analytical device according to a first embodiment of the present invention.
Figure 2:
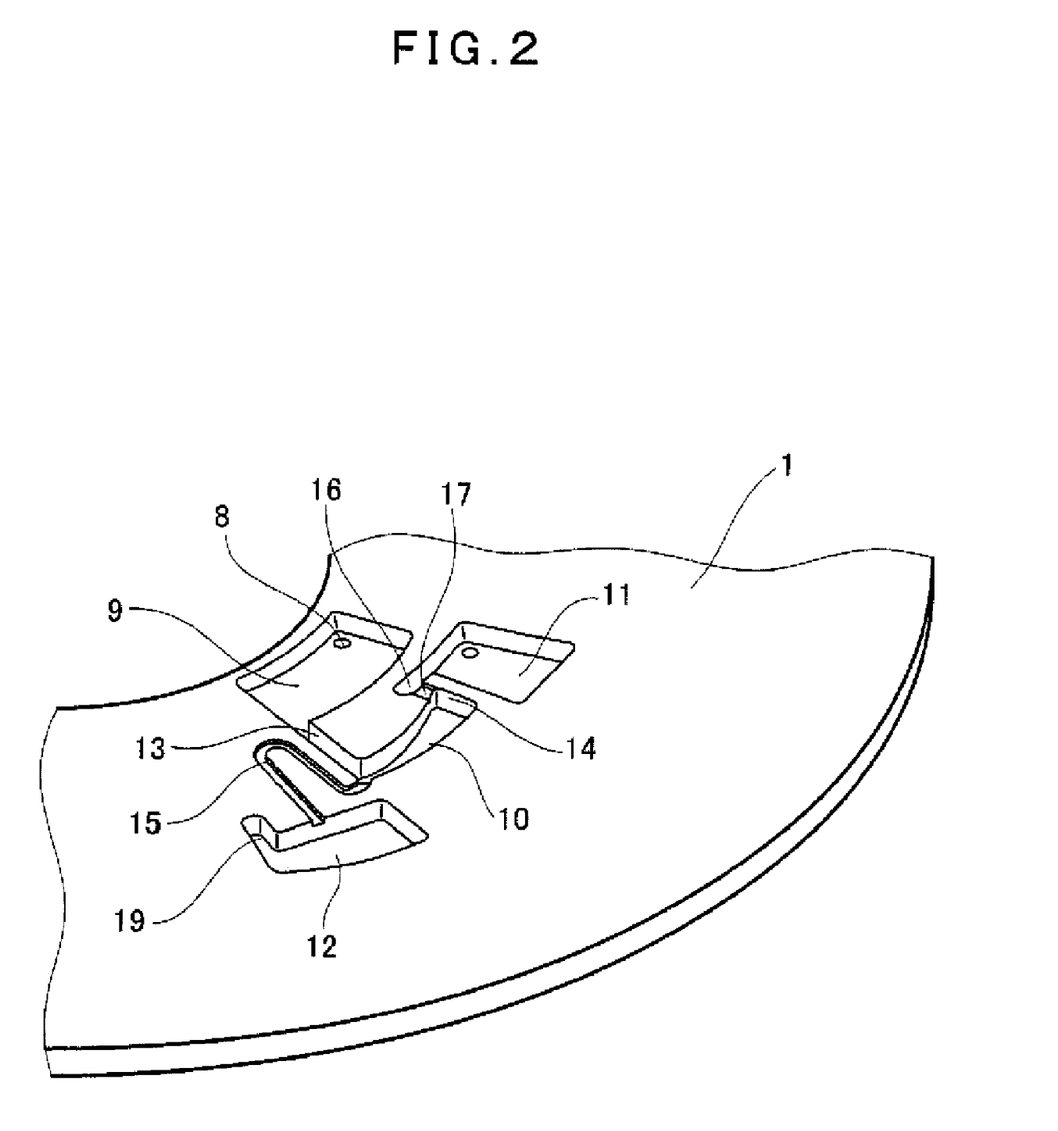
FIG. 2 is a perspective view of a base substrate according to the first embodiment.

FIG. 1 shows an analytical device according to the present invention. FIG. 2 shows a base substrate on which a micro channel, which is the major portion of the device, is formed.

Referring to FIG. 1, the analytical device of the present invention is composed of a base substrate 1 having micro channels 4a and 4b, a cover substrate 2 that closes the opening of the base substrate 1, and an adhesive layer 3.

Figure 3:
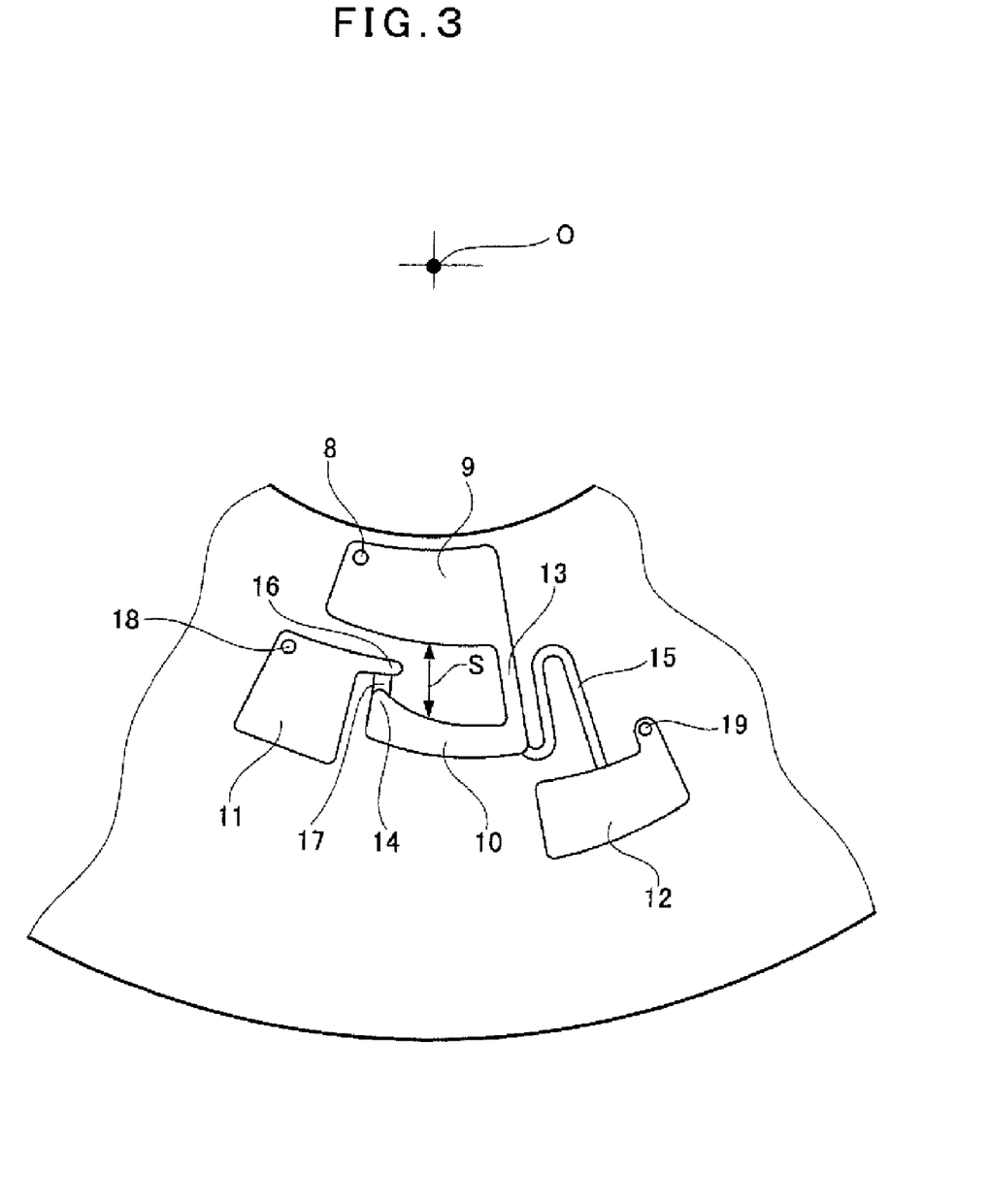
FIG. 3 is a plan view showing the micro channel configuration of the analytical device according to the first embodiment.

For the micro channels 4a and 4b formed on the base substrate 1, a concave-convex micro channel pattern as shown in FIG. 2 is fabricated by injection molding, so that a sample solution to be analyzed can be injected into the analytical device and transferred using centrifugal force and capillary force. In FIG. 3, the point O shows the rotating center of the analytical device when analysis is carried out.

In the present invention, transmitted light is radiated onto the micro channel 4a to optically analyze the reaction state of the sample solution to be tested and a reagent. In measuring, since the micro channel 4a is filled with a reaction solution 5 wherein the sample solution is allowed to react with the reagent, and the absorbance of the reaction solution 5 varies depending on the rate of reaction of the sample solution and the reagent, transmitted light is radiated onto the micro channel 4a from a light source 6, and change in intensity of light that has transmitted the reaction solution 5 can be measured by measuring the light intensity of the transmitted light in a light receiver 7, and the state of reaction can be analyzed.

Although the base substrate 1 and the cover substrate 2 are formed to have a thickness of 1 to 5 mm in the present invention, the present invention is not limited thereto, but the thickness may be a thickness so that the micro channels 4a and 4b can be formed. The shapes of the base substrate 1 and the cover substrate 2 are also not specifically limited, but the shape to meet the purpose of use, for example, sheet, plate, bar and other complicated shapes can also be used.

Although plastics are used as the materials for the base substrate 1 and the cover substrate 2 in the present invention because of ease of forming, high productivity, and low prices thereof, the present invention is not limited thereto as long as the materials can be joined, such as glass, silicon wafers, metals and ceramics.

Although a hydrophilic treatment is performed on the base substrate 1 having the micro channels 4a and 4b, and the cover substrate 2 to reduce the viscous resistance in the micro channels 4a and 4b to facilitate the transfer of fluid in the present invention, hydrophilic materials, such as glass may be used, or hydrophilic agents such as surface-active agents, hydrophilic polymers, and silica-gel powder may be used during forming to impart hydrophilic properties to the surface of the material. Examples of hydrophilic treating methods include surface treatment methods using active gas, such as plasma, corona, ozone and fluorine, and a surface treatment by surface-active agents. Here, the hydrophilic property means a property wherein the contact angle with water is less than 90°, preferably less than 40°.

Although an adhesive is used to join the base substrate 1 and the cover substrate 2 in the present invention, joining methods, such as fusion joining and anode joining may also be used depending on materials to be used.

Next, the micro channel configuration of the analytical device and the sample solution transferring process according to the first embodiment of the present invention described above will be described.

FIG. 3 is a plan view showing the micro channel configuration of the analytical device according to the first embodiment. FIGS. 4A to 4D are diagrams showing the sample solution transferring process according to the first embodiment of the present invention.

As shown in FIG. 2, the micro channel of the analytical device of the present invention is composed of a liquid accommodating chamber 9 for injecting and accommodating a sample solution; a volume measuring chamber 10 for measuring and holding a constant quantity of the sample solution; an overflowing chamber 11 for receiving the sample solution having a volume exceeding the volume of the volume measuring chamber 10; and a measuring cell 12 for transferring the sample solution measured in the volume measuring chamber 10, allowing the sample solution to react with a reagent, and measuring the absorbance of the solution. Although omitted in the present embodiment here, a separating chamber for separating cytoplasm, or a mixing chamber for diluting and mixing the sample solution may also be provided between the volume measuring chamber 10 and the measuring cell 12.

Although the liquid accommodating chamber 9, the volume measuring chamber 10, the overflowing chamber 11, and the measuring cell 12 are formed to have a depth of 0.3 mm to 2 mm in the present invention, the thickness may be adjusted depending on conditions for measuring the quantity or absorbance of the sample solution (light path length, measured wavelengths, reaction concentration of the sample solution, the kind of a reagent, etc.).

Figure 4A:
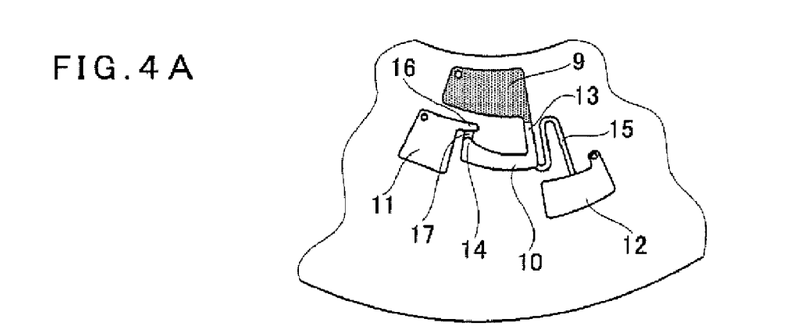
FIG. 4A is a process diagram of a transferring process according to the first embodiment.
Figure 4B:
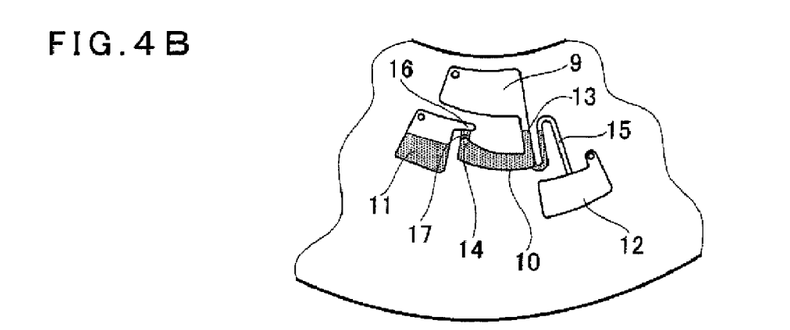
FIG. 4B is a process diagram of the transferring process according to the first embodiment.

The liquid accommodating chamber 9 is connected to the volume measuring chamber 10 via a connecting path 13, and the sample solution can be transferred to the volume measuring chamber 10 as shown in FIG. 4B, by injecting and accommodating the sample solution through an injecting port 8, and rotating the analytical device as shown in FIG. 4A.

Although the depth of the connecting path 13 is the same as those of the liquid accommodating chamber 9 and the volume measuring chamber 10 in the present invention, the connecting path 13 may have a capillary shape having a depth of 50 µm to 200 µm by providing the volume measuring chamber 10 with an air hole.

The volume measuring chamber 10 is connected to a flow-in port 16 of the overflowing chamber 11 disposed inward from the volume measuring chamber 10 in the radial direction via a capillary flow path 17, from an overflowing port 14 located on the innermost point of the volume measuring chamber 10 in the radial direction; and connected to the measuring cell 12 via a connecting path 15 from the outermost point of the volume measuring chamber 10 in the radial directions In the overflowing chamber 11, an air hole 18 is formed to facilitate the flow of the sample solution into the chamber. An air hole 19 is also formed in the measuring cell 12 to facilitate the flow of the sample solution through the connecting path 15.

The wall surface located inside the analytical device in the radial direction among the wall surfaces composing the volume measuring chamber 10 is formed so that the location in the radial direction approaches the rotation center from the flow-in port of the sample solution in the volume measuring chamber 10 toward the overflowing port 14.

The connecting path 15 has a siphon shape with a curved tube disposed inward from the distance between the flow-in port 16 of the overflowing chamber 11 and the capillary flow path 17, in relation to the rotation center of the analytical device. Although the connecting path 15 is formed to have a width of 0.5 mm to 2 mm, and a depth of 50 µm to 200 µm in the present invention, the present invention is not limited thereto as long as the connecting path 15 can be filled with the sample solution by capillary force.

By thus connecting the volume measuring chamber 10 with the measuring cell 12, even if the sample solution accommodated in the liquid accommodating chamber 9 is transferred to and filled in the volume measuring chamber 10 by the rotation of the analytical device, as shown in FIG. 4B, the sample solution in the connecting path 15 is filled only to the location corresponding to the distance in the radial direction from the rotation center of the analytical device to the interface between the flow-in port 16 of the overflowing chamber 11 and the capillary flow path 17.

Figure 4C:
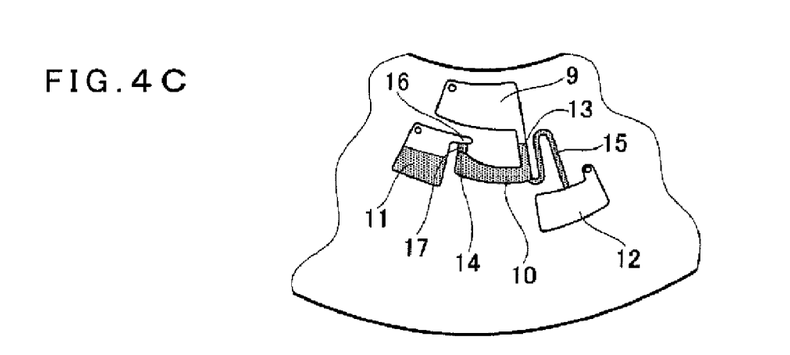
FIG. 4C is a process diagram of the transferring process according to the first embodiment.

When the operation of the analytical device is stopped after the completion of filling of the volume measuring chamber 10, as shown in FIG. 4C, capillary force acts in the connecting path 15 and the sample solution is filled to the inlet of the measuring cell 12. At this time, since the measuring cell 12 has a large depth, and capillary force is extremely smaller than that of the connecting path 15, the sample solution does not flow into the measuring cell 12.

Figure 4D:
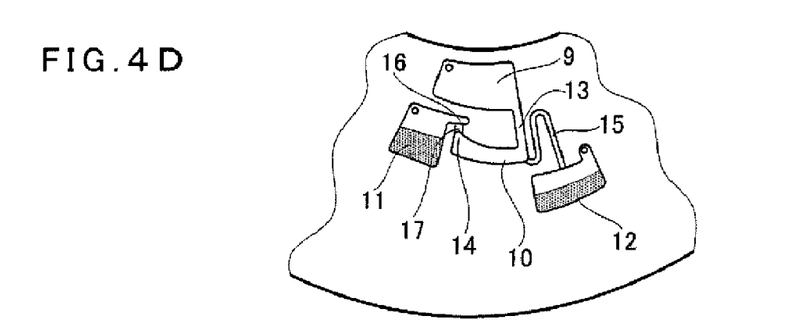
FIG. 4D is a process diagram of the transferring process according to the first embodiment.

After the connecting path 15 is filled, the analytical device is operated again to transfer the sample solution held in the volume measuring chamber 10 into the measuring cell 12 by the siphon effect as shown in FIG. 4D.

In the present invention, the shape of the wall surface positioned inside the analytical device in the radial direction among the wall surfaces composing the volume measuring chamber 10 is formed so as to enter inward in the radial direction from the vicinity of the connecting path 13 of the measuring chamber 10 toward the vicinity of the overflowing port 14. Specifically, by forming the wall surface positioned inside the analytical device in the radial direction among the wall surfaces composing the volume measuring chamber 10 so that the location in the radial direction approaches the rotation center as the sample solution forwards from the flow-in port of the volume measuring chamber 10 toward the overflowing port, since the air in the volume measuring chamber 10 is selectively discharged toward the overflowing port 14 when the sample solution is transferred from the liquid accommodating chamber 9, the fluctuation in measuring the sample solution due to mixing of the air when filling the volume measuring chamber 10 is decreased.

In the present invention, the capillary flow path 17 is formed to have a depth of 50 µm to 200 µm. Thus, since the liquid surface is stabilized at the location corresponding to the distance in the radial direction from the flow-in port 16 of the overflowing chamber 11 to the interface of the capillary flow path 17 when the analytical device is rotated, and the sample solution is trapped in the capillary flow path 17 by the capillary force of the capillary flow path 17 when the rotation of the analytical device is slowed down or stopped, the flow of the sample solution into the overflowing chamber 11 can be prevented, and accurate volume measurement can be feasible. In addition, since the sample solution trapped in the capillary flow path 17 is returned to the volume measuring chamber 10 by the centrifugal force during the following rotation, all the measured sample solution can be transferred to the following process.

Second Embodiment

Figure 5:
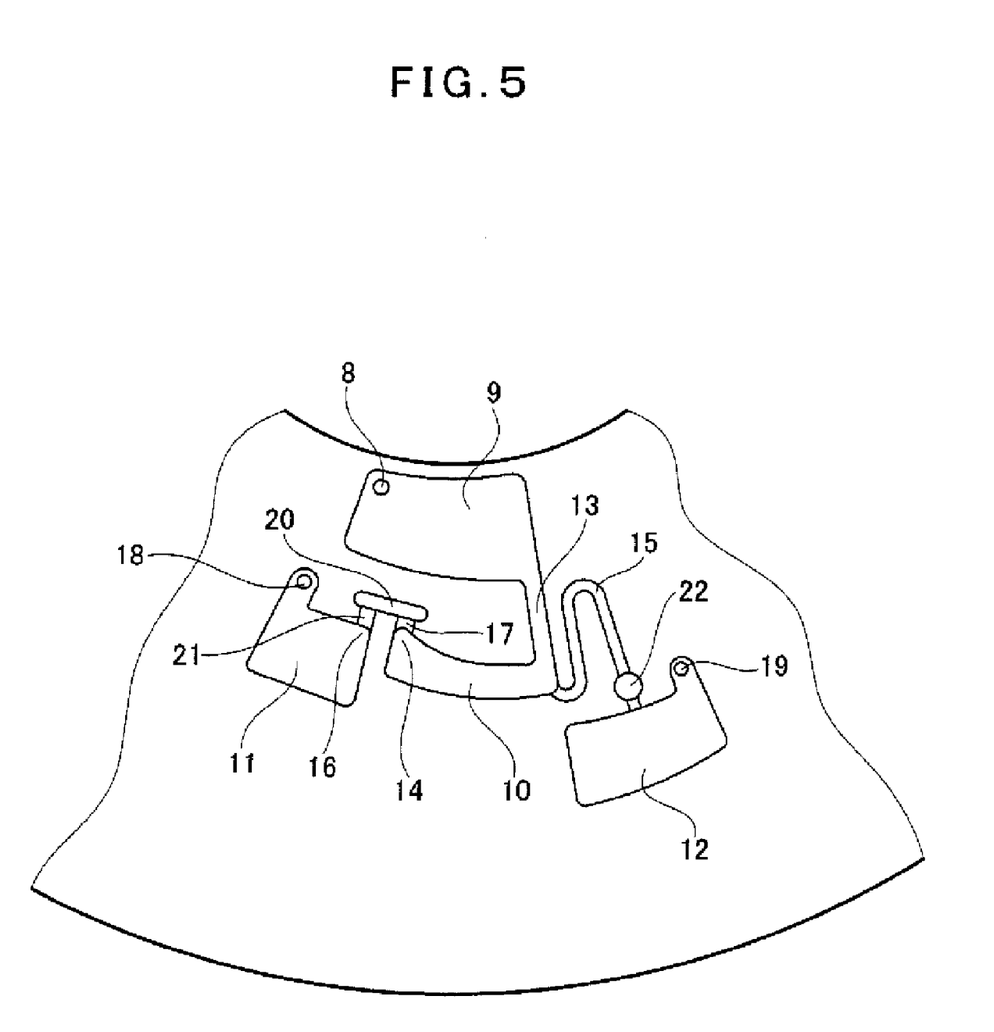
FIG. 5 is a plan view showing the micro channel configuration of an analytical device according to a second embodiment.
Figure 6:
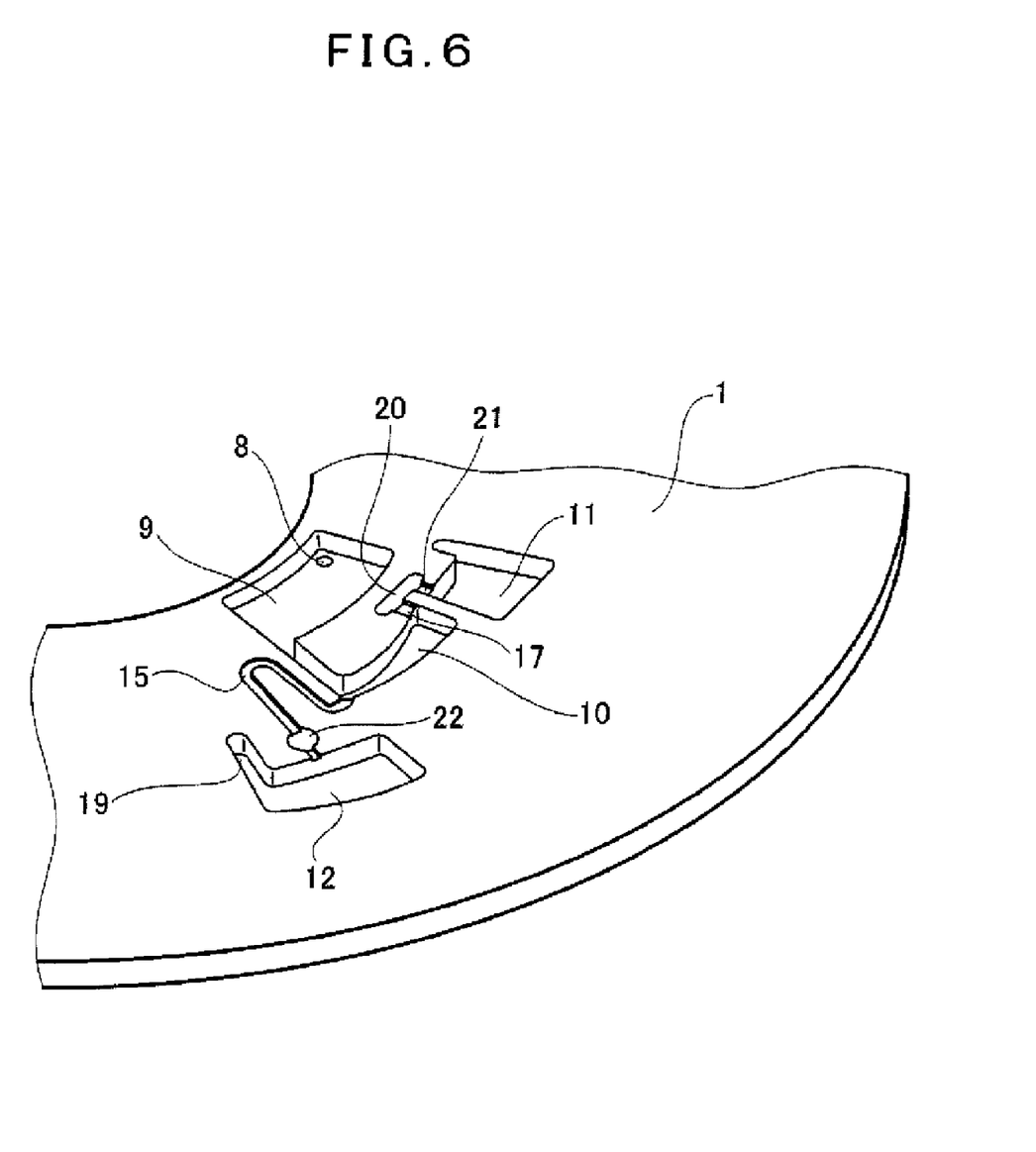
FIG. 6 is a perspective view of a base substrate according to the second embodiment.

FIG. 5 shows an analytical device according to the second embodiment of the present invention. FIG. 6 shows a base substrate wherein a micro channel, which is an essential part, is formed.

In FIG. 5, what is different from the first embodiment is that an overflow controlling chamber 20 is provided between an overflowing port 14 of a volume measuring chamber 10 and a flow-in port 16 of an overflowing chamber 11, and the flow-in port 16 of the overflowing chamber 11 is connected to the overflow controlling chamber 20 via a capillary flowing path 21 having a depth of 50 µm to 200 µm.

The overflow controlling chamber 20 is disposed inward in the radial direction from the volume measuring chamber 10 and the overflowing chamber 11, and has a depth of 0.3 mm to 2 mm as shown in FIG. 6. With such a configuration, even when the surface tension of the sample solution that has flowed into the overflowing chamber 11 is low, the sample solution is trapped in the capillary flowing path 21 by the capillary force of the capillary flowing path 21 when the rotation of the analytical device is stopped; therefore, the back-flow of the sample solution into the volume measuring chamber 10 can be suppressed.

Similarly, by connecting a connecting path 15 and the volume measuring chamber 10 with a measuring cell 12 via a capillary valve 22 having a depth of 0.3 mm to 2 mm provided between the measuring cell 12 and the location corresponding to the distance in the radial direction outward from the outermost point of the volume measuring chamber 10, since there is the capillary valve 22 having an extremely small capillary force, the sample solution transferred into the measuring cell 12 can be returned only to the flow-out port of the capillary valve 22 by the capillary force, and the back-flow of the sample solution into the volume measuring chamber 10 can be suppressed.

Third Embodiment

Figure 7:
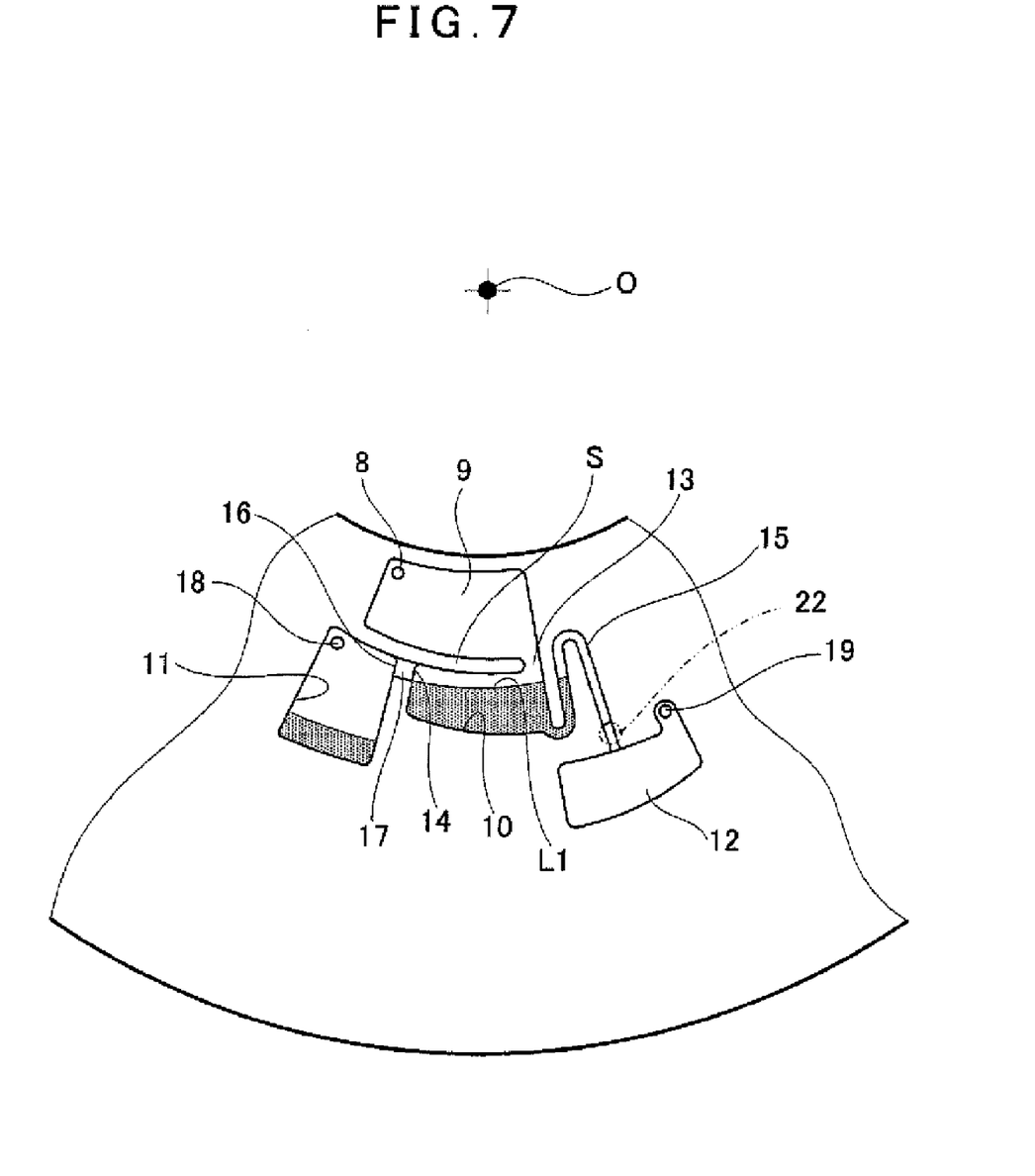
FIG. 7 is a configuration diagram of an analytical device according to a third embodiment.

FIG. 7 shows an analytical device according to the third embodiment of the present invention.

Although a flow-in port 16 of an overflowing chamber 11 is disposed inward from an overflowing port 14 of a volume measuring chamber 10 in the radial direction, and the flow-in port 16 of the overflowing chamber 11 is connected to the overflowing port 14 of the volume measuring chamber 10 by a capillary path 17 in the first embodiment as shown in FIG. 3, in the third embodiment, as shown in FIG. 7, the flow-in port 16 of the overflowing chamber 11 is disposed in the same radial direction as the overflowing port 14 of the volume measuring chamber 10, and the flow-in port 16 of the overflowing chamber 11 is connected to the overflowing port 14 of the volume measuring chamber 10 by the capillary path 17. The other configuration is the same as the configuration shown in FIG. 3, and the parts having the same functions are denoted by the same symbols. L1 in the volume measuring chamber 10 in the drawing shows the liquid surface in the state wherein a specified quantity of the sample solution that has been flowed from a liquid accommodating chamber 9 is sampled in the volume measuring chamber 10. The excessive sample solution that has been flowed from the liquid accommodating chamber 9 into the volume measuring chamber 10 flows into the overflowing chamber 11 exceeding the set level of the capillary path 17, so that the sampling quantity of the sample solution in the volume measuring chamber 10 becomes the specified quantity.

With such a configuration, when FIG. 3 and FIG. 7 are compared, the space S seen between the outer circumferential side of the liquid accommodating chamber 9 and the inner circumferential side of the volume measuring chamber 10 can be reduced in the case of the third embodiment shown in FIG. 7. In FIG. 3, although the case wherein one measuring cell 12 is provided within a limited dimension of the analytical device in the radial direction is illustrated, in the third embodiment shown in FIG. 7, a larger number of measuring cells 12 can be provided compared with the case wherein the dimension of the analytical device in the radial direction is the same as in FIG. 3. If the number of the measuring cells 12 may be the same as in FIG. 3, the size of the analytical device can be reduced.

Also in this case, in the same manner as the second embodiment shown in FIG. 5, a capillary valve 22 can be installed in the middle of a connecting path 15 between the measuring cell 12 and the location outside the outermost point of the volume measuring chamber 10 in the radial direction, as indicated by the phantom line, to connect the volume measuring chamber 10 with the measuring cell 12.

Fourth Embodiment

Figure 8:
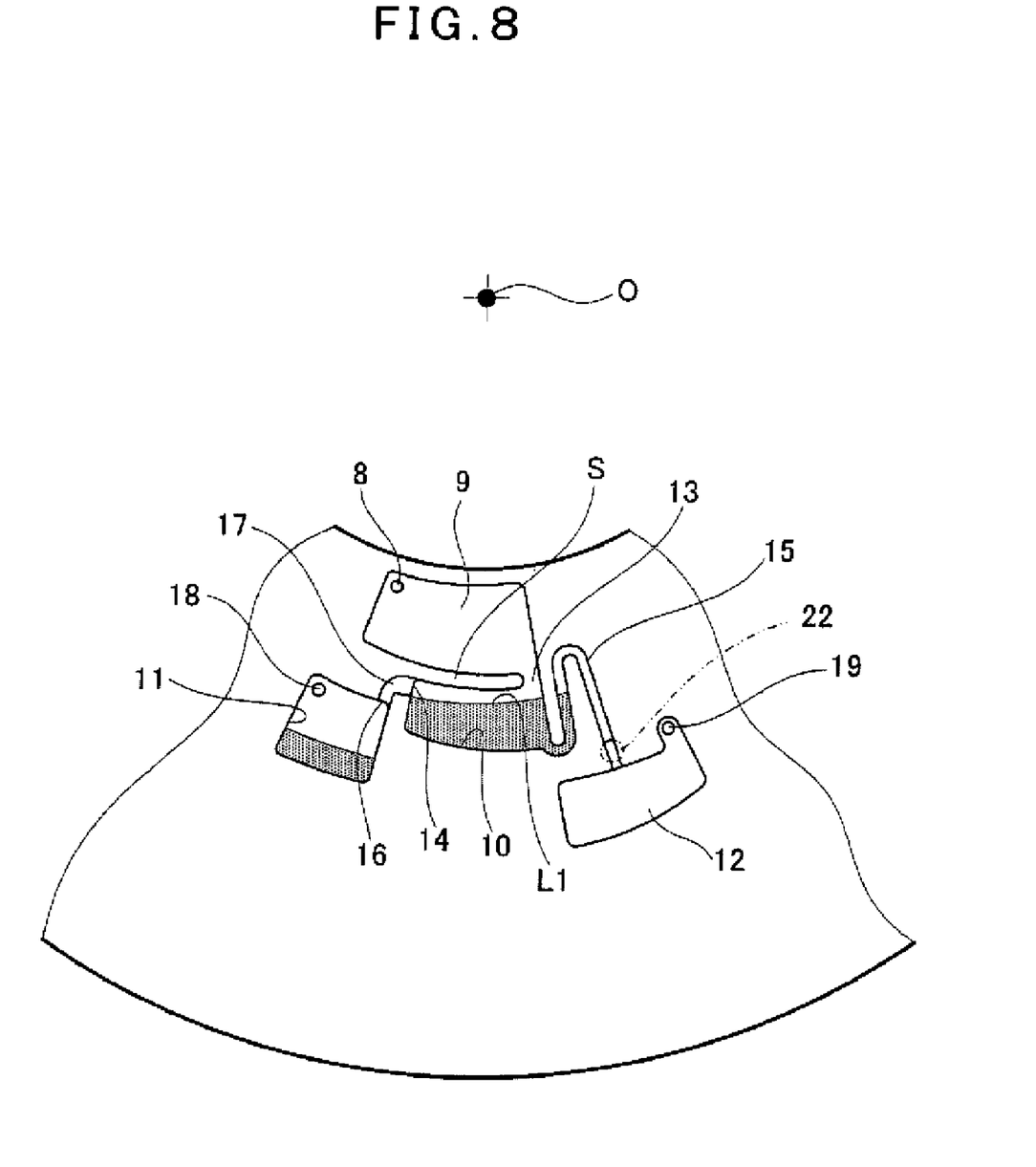
FIG. 8 is a configuration diagram of an analytical device according to a fourth embodiment.

FIG. 8 shows an analytical device according to the fourth embodiment of the present invention.

In the first embodiment, although a flow-in port 16 of an overflowing chamber 11 is disposed inward from an overflowing port 14 of a volume measuring chamber 10 in the radial direction and the flow-in port 16 of the overflowing chamber 11 is connected to the overflowing port 14 of the volume measuring chamber 10 by a capillary path 17 as shown in FIG. 3, in the fourth embodiment, as shown in FIG. 8, the flow-in port 16 of the overflowing chamber 11 is disposed outward from the overflowing port 14 of the volume measuring chamber 10 in the radial direction and the flow-in port 16 of the overflowing chamber 11 is connected to the overflowing port 14 of the volume measuring chamber 10 by the capillary path 17. The other configuration is the same as the configuration shown in FIG. 3, and the parts having the same functions are denoted by the same symbols. L1 in the volume measuring chamber 10 in the drawing shows the liquid surface in the state wherein a specified quantity of the sample solution that has been flowed from a liquid accommodating chamber 9 is sampled in the volume measuring chamber 10. The excessive sample solution that has been flowed from the liquid accommodating chamber 9 into the volume measuring chamber 10 flows into the overflowing chamber 11 exceeding the set level of the capillary path 17, so that the sampling quantity of the sample solution in the volume measuring chamber 10 becomes the specified quantity.

With such a configuration, when FIG. 3 and FIG. 8 are compared, the space S seen between the outer circumferential side of the liquid accommodating chamber 9 and the inner circumferential side of the volume measuring chamber 10 can be reduced in the case of the fourth embodiment shown in FIG. B. In FIG. 3, although the case wherein one measuring cell 12 is provided within a limited dimension of the analytical device in the radial direction is illustrated, in the fourth embodiment shown in FIG. 8, a larger number of measuring cells 12 can be provided compared with the case wherein the dimension of the analytical device in the radial direction is the same as in FIG. 3. If the number of the measuring cells 12 may be the same as in FIG. 3, the size of the analytical device can be reduced.

Also in this case, in the same manner as the second embodiment shown in FIG. 5, a capillary valve 22 can be installed in the middle of a connecting path 15 between the measuring cell 12 and the location outside the outermost point of the volume measuring chamber 10 in the radial direction, as indicated by the phantom line, to connect the volume measuring chamber 10 with the measuring cell 12.

In each of the above-described embodiments, the sample solution injected into and accommodated in the liquid accommodating chamber 9 is a biological fluid, such as blood and diluted blood.

The present invention can contribute to the acceleration of the component analysis processing and the improvement of analytical accuracy of biological fluids.

What is claimed is:

1. A centrifugal analytical device comprising a rotary base which includes:
   a liquid accommodating chamber for accommodating a quantity of a sample solution required for analyzing;
   a volume measuring chamber for retaining a specified quantity of a sample solution, connected to the liquid accommodating chamber by a connecting path, and located radially outside the liquid accommodating chamber; and
   an overflow chamber connected to the volume measuring chamber for accommodating a quantity of a sample solution exceeding the specified quantity, wherein
   the volume measuring chamber includes a radially inner wall surface and an outer wall surface located radially outside the inner wall, a sample solution flow-in port and an overflowing port separately located in the inner wall surface of the volume measuring chamber, the sample solution flow-in port for permitting a sample solution from the liquid accommodating chamber to flow via the connecting path, for passing sample solution exceeding in volume the specified quantity of the volume measuring chamber through the overflow port to the overflow chamber, the flow-in port of the overflow chamber is radially inward from the overflow port of the volume measuring chamber, and connected to the overflow port by a capillary flow path, and the inner wall of the volume measuring chamber decreases in radial distance from the rotational center of the rotary base from the sample solution flow-in port toward the overflowing port.

2. The centrifugal analytical device according to claim 1, wherein the overflowing port of the volume measuring chamber is connected to the flow-in port of the overflowing chamber via an overflow controlling chamber which is radially inward from the volume measuring chamber and the overflowing chamber.

* * * * *